United States Patent [19]

Gaskin

[11] Patent Number: 5,629,314

[45] Date of Patent: May 13, 1997

[54] METHODS AND COMPOSITIONS FOR REDUCING PYRIMIDINE PHOTOPRODUCTS

[76] Inventor: Frances C. Gaskin, 298 State St., Albany, N.Y. 12210

[21] Appl. No.: 440,626

[22] Filed: May 15, 1995

[51] Int. Cl.$^6$ .......................... A61K 31/505; A61K 7/42
[52] U.S. Cl. ..................... 514/256; 424/59; 424/60; 514/269; 514/937; 514/938; 514/939; 514/944; 514/969
[58] Field of Search .................. 424/59, 60; 514/256, 514/269, 937, 938, 939, 944, 969

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,806,344 | 2/1989 | Gaskin | 424/59 |
| 5,256,403 | 10/1993 | Gaskin | 424/59 |

OTHER PUBLICATIONS

John Clark Sutherland, et al; Two–Dimensional, Computer–Controlled Film Scanner: Quantitation of Fluorescence from Ethidum Bromide–Stained DNA Gels, Analytical Biochemistry 139, 390–399 (1984).
W. L. Carrier and R. B. Setlow; Endonuclease from Micrococcus Luteus Which Has Activity Toward Ultraviolet–Irradiated Deoxyribonucleic Acid: Purification and Properties; Journal of Bacteriology, Apr. 1970 pp. 178–186.
John Jagger; A Small and Inexpensive Ultraviolet Dos–Rate Meter Useful in Biological Experiments; Radiation Research 14, 394–403 (1961).
Steven E. Freeman, et al., *Pyrimidine Dimer Formation in Human Skin*, Photochemistry and Photobiology, vol. 46 (No. 2):207–212 (1987).
Douglas E. Brash & William A. Haseltine, *UV–induced Mutation Hotspots Occur at DNA Damage Hotspots*, Nature, vol. 298:189 (1982).
Steven E. Freeman, et al., *Wavelength Dependence of Pyrimidine Dimer Formation in DNA of Human Skin Irradiated in situ with Ultraviolet Light*, Proc. Nat'l. Acad. Sci. USA, vol. 86:5605–5609 (1989).
John C. Sutherland, et al., *Unidirectional Pulsed–Field Electrophoresis of Single and Double–Stranded DNA in Agarose Gels; Analytical Expressions Relating Mobility and Moceluar Length and Their Application in the Measurement of Strand Breaks*, Analytical Biochemistry, vol. 162:511–520 (1987).
John C. Sutherland, et al., *Lesion Measurement in Non–Radioactive DNA by Quantitive Gel Electrophoresis*, DNA Damage and Repair in Human Tissues, 45–61 (1990).
Steven E. Freeman, et al., *Quantitation of Radiation, Chemical or Enzyme–Induced Single Strand Breaks in Nonradioactive DNA by Alkaline Gel Electrophoresis: Application to Pyrimidine Dimers*, Analytical Biochemistry vol. 158:119–129 (1986).
Betsy M. Sutherland and Alice G. Shih, *Quantitation of Pyrimidine Dimer Contents of Nonradioactive Deoxyribonucleic Acid by Electrophoresis in Alakaline Agarose Gels*, Biochemistry, vol. 22:745–749 (1983).

John C. Sutherland, et al., *Quantitative Electronic Imaging of Gel Fluorescence with CCD Cameras: Applications in Molecular Biology*, Bio Techniques, vol. 10 (No. 4):492–497 (1991).
F.E. Quaite, Betsy M. Sutherland & John C. Sutherland, *Action Spectrum for DNA Damage in Alfalfa Lowers Predicted Impact of Ozone Depletion*, Nature, vol. 358:576–578 (1992).
Paula V. Bennett & Betsy M. Sutherland, *Quantitative Detection of Single–Copy Genes in Nanogram Samples of Human Genomic DNA*, Bio Techniques, vol. 15 (No. 3):520–525 (1993).
F.E. Quaite, John C. Sutherland & Betsy M. Sutherland, *Isolation of High–Molecular–Weight Plan DNA for Damage Quantitation: Relative Effects of Solar 297 nm UVB and 365 nm Radiation*, Plant Molecular Biology, vol. 24: 475–483 (1994).
R. Cadi, et. al., *Protective Effect of Flavopherol Against Lipid Peroxidation and Experimental UV B–induced Carcinogenesis in the Hairless Mouse*, Nouv. Dermatol.
John C. Sutherland, *Electronic Imaging of Electrophertic Gels and Blots*, VCH Publishers, 1–42 (1993).
John C. Sutherland, et al., *Two Dimensional, Computer Controlled Film Scanner: Quantitation of Fluorescence from Ethidium Bromide Stained DNA Gels*, Nal. Biochem, 139:390–399 (1984).
W.L. Carrier, *Endonuclease from Micrococcus Luteus which has Activity Toward Ultraviolet–Irradiated DNA: Purification and Properties*, J. Bact. 102:178–186 (1970).
J. Jagger, *A Small and Inexpensive Ultraviolet Dose–Rate Meter Useful in Biological Experiments*, Radiat. Res. 14:394–403 (1961).

*Primary Examiner*—Shelley A. Dodson

[57] ABSTRACT

This invention is directed to a method for reducing pyrimidine photoproducts comprising applying an effective amount of melanin to human skin prior to exposure to ultraviolet rays, wherein said melanin is in a vehicle suitable for topical application and measuring the amount of pyrimidine photoproducts as compared to a control sample. Another embodiment of this invention is where the vehicle is an ointment, cream or lotion. For the purpose of this invention, measuring also means determining, and/or quantifying.

This invention is also directed to a method for reducing pyrimidine photoproducts comprising applying an effective amount of melanin and solubilizing substance to human skin prior to exposure to ultraviolet rays, wherein said substance for solubilizing melanin is selected from the group consisting of triethanolamine and trypsin, wherein said solubilizing substance is present in an amount sufficient to solubilize the melanin thereby producing melanin solubilized by said substance, wherein said melanin and solubilizing substance is in a vehicle suitable for topical application and measuring the amount of pyrimidine photoproducts as compared to a control sample. Another embodiment of this invention is where the vehicle is an ointment, cream or lotion. For the purpose of this invention, measuring also means determining, and/or quantifying.

8 Claims, 4 Drawing Sheets

(PANEL A)

(PANEL B)

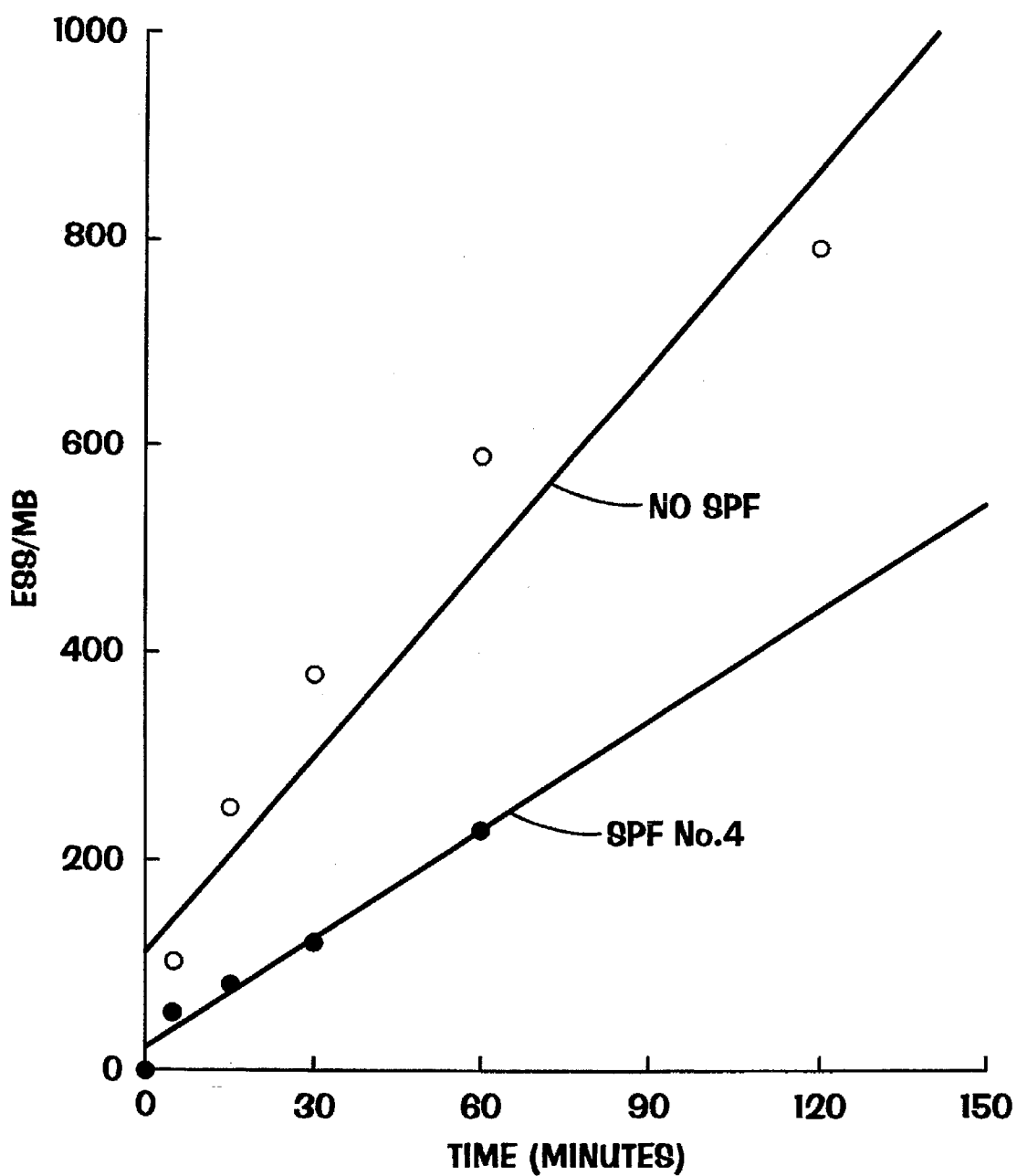

METHODS AND COMPOSITIONS FOR REDUCING PYRIMIDINE PHOTOPRODUCTS

BACKGROUND OF THE INVENTION

The Government may own certain rights in the present invention pursuant to the Office of Health and Environmental Research, USDOE and by Cooperative Research and Development Agreement BNL-C-94-21.

FIELD OF THE INVENTION

The present invention is directed to a method for reducing pyrimidine photoproducts in humans after exposure to ultraviolet radiation.

BACKGROUND OF THE PRESENT INVENTION

The sensitivity of the human skin to the ultraviolet (UV) rays (UVR) of the sun is determined by the amount of the pigment, "melanin," contained within the skin. Many individuals with fair or light/white complexions (Skin Types I, II, III) burn because they do not produce sufficient melanin to protect the skin against sunburn. Moderately brown to dark skinned persons (Skin Types IV, V, VI) are not entirely protected form the deleterious effects of solar radiation. The different Skin Type classifications are characterized as follows:

Skin Type I: burns easily (freckles) and never tans;

Skin Type II: burns easily and tans minimally;

Skin Type III: burns moderately and tans gradually;

Skin Type IV: burns minimally and tans well; and

Skin Types V and VI: tans very well and rarely burns.

In addition to sunburn, long-term exposure to the sun, particularly for individuals who do not produce sufficient melanin such as Skin Types I, II, III can lead to premature aging of the skin and cutaneous cancer, usually basal cell, squamous cell carcinomas and malignant melanomas. Dark skinned persons do develop skin cancer but in small percentages, for example, malignant melanomas may occur in areas of the body where melanin levels are low, such as the palmar surfaces of the hands and plantar surfaces of the feet. Conditions such as allergic reactions, coarseness, dryness, mottling, flaccidity and blemishes are also effects of long-term exposure. To obviate these detrimental effects, experts in the field have suggested sun protection formulas having various combinations and percentages of chemical, physical and natural sunscreens, with the sun protective factor (SPF) ranging from 2 to 30 (minimal sun protection=2 and maximum sun protection=30).

Further, melanin precursors (i.e. tyrosine, tyrosinase and 3,4-Dihydroxy Phenylalanine (DOPA)) are included in suntan preparations to stimulate the production of melanin. Yet, each year these harmful or life-threatening toxicities are becoming more widespread because the problem still exists for those persons who do not genetically possess sufficient melanocytes (pigment cells) to produce enough melanin.

The pigment cell colors the skin by injecting melanosomes into keratinocytes. The keratinocyte carries pigment to the stratum corneurn where it is shed as melanin dust. Melanin provides effective protection against actinic damage of the sun. Notably, there exists an increased correlation between skin sensitivity to UV radiation and melanin content. The degree of sunburn reaction, prevalence of abnormal photosensitivity and the degenerative (aging) and neoplastic changes are reduced with increasing melanin pigmentation. This increased relationship is correlated to the distribution of melanosomes and quantity of melanin in the epidermis. The SPF estimates of melanin have been cited as 1.0–4.3 to 5 for Skin Types I through Skin Types V and VI, respectively.

The photoprotective role of melanin is related to its physical and biochemical properties. Melanin (a) scatters and degrades radiation to heat; (b) absorbs the radiation and promotes immediate oxidation reaction, and (c) quenches free radicals generated by UV radiation. Further, melanin in the human epidermis functions as a stable free radical. Because of its polyquinoid nature, melanin acts as an electron exchange polymer and therefore is capable of undergoing immediate photo-oxidation or darkening reaction. Melanin quenches the formulation of other types of damaging free radicals in the human epidermis upon exposure to UV radiation. Thus melanin serves as a scavenger for damaging non-melanin free radicals which may significantly contribute to its photoprotective role in individuals of Skin Types IV, V and VI.

The exposure to UV radiation itself produces a phototherapeutic advantage. Subsequent to three UV radiation exposures, Skin Types IV, V, VI become less likely to sunburn. However, Types I, II, III individuals develop very few melanized melanosomes. A melanin filter never develops in the stratum corneum resulting in an absence of melanin dust in the epidermis. Therefore, the need exists for the formulation of the topical application of melanin to provide an added amount of melanin in the skin to protect the human skin from the UV rays of the sun. Yet, dissolving melanin in solution or otherwise distributing melanin in a mixture suitable for topical application for delivery of melanin into the skin has been a difficult problem in the past. This problem was solved with U.S. Pat. Nos. 5,256,403 and 4,806,344.

The instant invention is significant in that it provides evidence at the molecular level of the effect of shielding of DNA against skin cancer-inducing lesions by sunscreening agents.

The instant invention, which is directed to a method for reducing pyrimidine photoproducts, uses methods and compositions previously described in U.S. Pat. Nos. 5,256,403 and 4,806,344 (which include natural sunscreening preparations produced by Frances Christian Gaskin, Inc.); however the claimed invention is not limited to using only the sunscreen preparations taught in U.S. Pat. Nos. 5,256,403 and 4,806,344 (herein incorporated by reference). Briefly, U.S. Pat. No. 4,806,344 teaches a composition and method of dissolving melanin in a composition for the purpose of photoprotection of human skin from exposure to ultraviolet radiation.

U.S. Pat. No. 5,256,403 teaches a solubilized melanin based compositions. The compositions consist of melanin, the active ingredient, and a substance to solubilize the melanin, blended together in a vehicle suitable for topical application.

The effects on environmental carcinogens, such as the increased levels of UVB in the biosphere resulting from ozone depletion, is a major human health concern. The natural sunscreening preparations produced by Frances Christian Gaskin, Inc. provide excellent protection to human skin against increased levels of the highly dangerous carcinogen, UVB. This invention is not limited to using sunscreen preparations produced by Frances C. Gaskin, Inc. (FCG) to reduce pyrimidine photoproducts but the inventor does prefer to use the sunscreen preparations as created by Frances C. Gaskin, Inc. to achieve this goal.

BRIEF DESCRIPTION OF THE DRAWINGS

FIG. 3 Test of FCG SPF #4 on Lambda DNA Using a FS20 Sunlamp (0.320 mA). See Experimental Set-up in Panel A, FIG. 1. Lambda DNA which is approximately 49.5 kilobases in size was used. The X-axis represents "Time" that Lambda n6 methanol-free DNA was exposed to a standard FS20 Fluorescent Sunscreen Tanning Lamp. The Y-axis represents Endonuclease Sensitive Sites (ESS) per mega bases (number of pyrimidine dimers per mega (million) bases).

Figure 1:
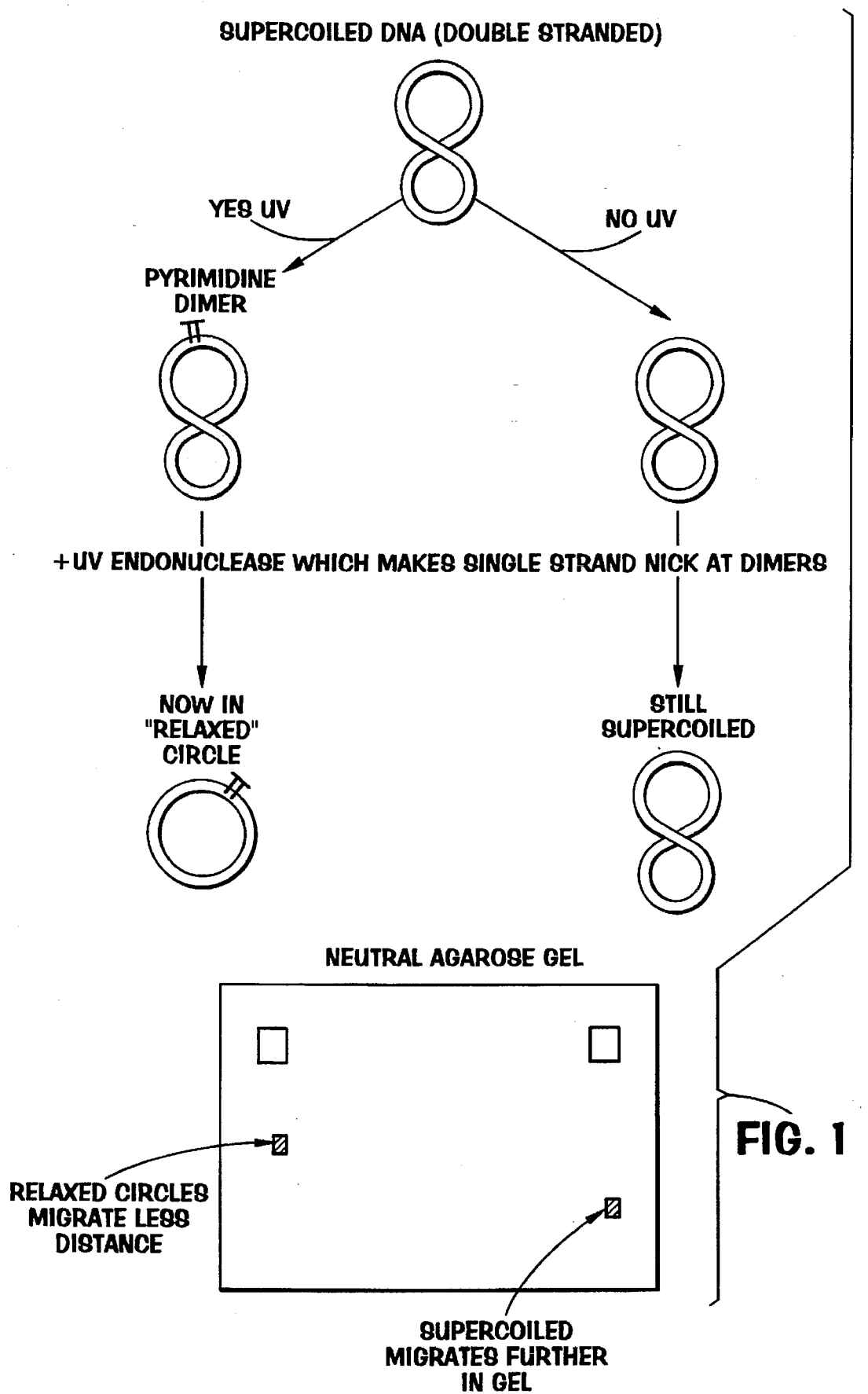
FIG. 1 Outline Depicting the Principles of Pyrimidine Dimer Determination by Alkaline Agarose Gel Method.

1 LANES 1-2 MOLECULAR WEIGHT MARKERS:

Lane 1: Molecular Weight Marker
Lane 2: Molecular Weight Marker

LANES 3-8: NO SUNSCREEN

Lane 3: No UV
Lane 4: No UV
Lane 5: 110 J/m$^2$
Lane 6: 165 J/m$^2$
Lane 7: 220 J/m$^2$
Lane 8: 275 J/m$^2$

LANES 9-12: SPF #4 (0.005 G/2.5 CM$^2$)

Lane 9: No UV
Lane 10: 165 J/m$^2$
Lane 11: 220 J/m$^2$
Lane 12: 275 J/m$^2$

LANES 13-17: FCG (1:500 DILUTION OF PURE FCG)

Lane 13: No UV
Lane 14: 165 J/m$^2$
Lane 15: 275 Jtm$^2$
Lane 16: 550 J/m$^2$
Lane 17: 825 J/m$^2$

LANES 18-20 MOLECULAR WEIGHT MARKERS:

Lane 18: Molecular Weight Marker
Lane 19: Molecular Weight Marker
Lane 20: Molecular Weight Marker

SUMMARY OF THE INVENTION

This invention is directed to a method for reducing pyrimidine photoproducts comprising applying an effective amount of melanin to human skin prior to exposure to ultraviolet rays, wherein said melanin is in a vehicle suitable for topical application and measuring the amount of pyrimidine photoproducts as compared to a control sample. Another embodiment of this invention is where the vehicle is an ointment, cream or lotion. For the purpose of this invention, measuring also means determining, and/or quantifying.

This invention is also directed to a method for reducing pyrimidine photoproducts comprising applying an effective amount of melanin and solubilizing substance to human skin prior to exposure to ultraviolet rays, wherein said substance for solubilizing melanin is selected from the group consisting of triethanolamine and trypsin, wherein said solubilizing substance is present in an amount sufficient to solubilize the melanin thereby producing melanin solubilized by said substance, wherein said melanin and solubilizing substance is in a vehicle suitable for topical application and measuring the amount of pyrimidine photoproducts as compared to a control sample. Another embodiment of this invention is where the vehicle is an ointment, cream or lotion. For the purpose of this invention, measuring also means determining, and/or quantifying.

DETAILED DESCRIPTION OF THE PREFERRED EMBODIMENTS

Ultraviolet (UV) radiation in sunlight induces short and long term damages in human skin such as sunburning, wrinkling, premature skin aging and skin cancers. Since melanomas arise from human melanocytes, effects of UV on primary human melanocytes are very important. Sunscreens protect human skin against UV damage, and melanin is a naturally occurring intracellular sunscreen. Melanin can also induce radicals upon exposure to UV, and these radicals may alter the kinds of DNA damage induced by UV exposure.

Solar radiation induces erythema, skin thickening and cancers in the skin of man. DNA is a suspected molecular target for the action of sunlight in damaging human skin. A major ultraviolet light-induced photoproduct in DNA is the cyclobutyl pyrimidine dimer formed between adjacent pyrimidines on the same DNA strand. Dimers have been implicated in the lethal, mutagenic, and tumorigenic effects of ultraviolet radiation in simple organisms and have been shown to be produced by UVB (290-320 nm) radiation in human skin. In addition to their potential intrinsic biological importance, dimers are easily quantitated and provide a useful dosimeter of damage of DNA in situ.

Melanin-based sunscreen preparations (MELANIN FCG and MELANIN PLUS) have been produced and patented which protect human skin against the deleterious effects of UV (U.S. Pat. Nos. 4,806,344 and 5,256,403). These preparations are used in the Examples below to study their effect on pyrimidine dimers and to determine if they reduce pyrimidine photoproducts.

Procedures have been developed for measuring the frequency and kinds of DNA damages induced by agents such as UV in nanogram quantities of non-radioactive DNA from human cells and skin (Freeman S. E. et al, *Quantitation of radiation-, chemical-, or enzyme-induced single strand breaks in nonradioactive DNA by alkaline gel electrophoresis: application to pyrimidine dimers*. Analyt. Biochem. 158:119–129 (1986); Freeman, S. E., et al. *Pyrimidine dimer formation in human skin*, Photochemistry and Photobiology, 46(2):207–212, 1987). The method allows detection of pyrimidine dimer levels as low as one per million bases in about 50 nanograms of non-radioactive DNA. The protocol is based on (1) the specific and quantitative induction of single strand breaks at dimers sites by UV endonuclease from *Micrococcus luteus* and (2) separation of the resulting cleaved, single stranded DNA as a function of molecular length by alkaline agarose electrophoresis. Thus, the method is sensitive enough to quantify one damage per two million bases for single strand breaks and damages affecting one DNA strand, and to quantify one damage per 100 million bases for double strand breaks. Sutherland et al has also developed methods for quantitating survival and mutation, including transformation, of human skin cells (Sutherland, et al, *Two dimensional, computer controlled film scanner: quantitation of fluorescence from ethidium bromide stained DNA gels*, Nal. Biochem., 139:390–399 (1984)). These methods have been applied to cultured human skin cells, including fibroblasts, keratinocytes and melanocytes, human skin biopsies and human skin in situ. The procedures have also been used to test the effect of sunscreens such as PABA (paraamino benzoic acid) on DNA damage and on cellular transformation of human skin cells.

Briefly, FIG. 1 describes the principles of pyrimidine dimer determination by the alkaline agarose gel method. DNA from skin or in situ (or in culture, in vitro, or in DNA sequences themselves) is exposed to UV radiation and then the DNA is extracted from the skin as described in standard DNA isolation protocols known to a person of ordinary skill in the art. DNA occurs in its supercoiled state (double stranded DNA) and pyrimidine dimers result in the DNA from exposing the DNA to UV radiation (pyrimidine dimers are defined as a type of DNA damage which links together two pyrimidines adjacent to each other on the same strand of DNA (i.e. CC, CT, TC, or TT)). The DNA is then treated with UV endonuclease (e.g. an endonuclease isolated from *Micrococcus luteus*) which makes a single strand nick adjacent to each pyrimidine dimer. UV endonuclease is prepared by the standard protocol of Carrier et al (Carrier, W. L. *Endonuclease from Micrococcus luteus which has activity toward ultraviolet-irradiated DNA: purification and properties*, J. Bact. 102:178–186 (1970). The DNA is no longer supercoiled and now appears in its "relaxed" circle form. The UV endonuclease creates nick adjacent to the dimer and from these nicks the number of *Micrococcus luteus* UV endonuclease sensitive sites per 1000 bases (ESS/kb) is determined (Sutherland, et al, *Two dimensional, computer controlled film scanner: quantitation of fluorescence from ethidium bromide stained DNA gels*, Nal. Biochem., 139:390–399 (1984)). The endonuclease treated or untreated DNA is denatured by treatment with alkali and electrophoresed on an alkaline agarose gel along with molecular weight standard markers. After denaturation, the single stranded DNAs are separated according to molecular length by electrophoresis in an alkaline agarose gel. The lane on the left of FIG. 1 depicts DNA not treated with UV endonuclease—DNA that contains dimers but was not treated with endonuclease migrates as a higher molecular length band. The lane on the right of FIG. 1 depicts the endonuclease treated DNA—the same DNA after UV endonuclease treatment migrates as a heterogeneous, lower molecular length band. The alkaline agarose gel protocol is detailed in depth in Freeman et al (Steven E. Freeman, et al., *Pyrimidine Dimer Formation in Human Skin, Photochemistry and Photobiology*, 46(2): 207–212 (1987) herein incorporated by reference).

DEFINITIONS

For the purpose of this invention, the following terms, words and phrases shall have the following meanings:

UV radiation: ultraviolet radiation photoproduct: any change or modification in DNA whereby the change is induced by light or any light source light: any source which includes fluorescence and ultraviolet dose of radiation: Joules/$m^2$; "J"

FCG Sunscreen: SPF #4, Melanin Plus, and Melanin FCG produced by Frances C. Gaskin Inc.

UVA radiation: wavelengths between 320–400 nm

UVB radiation: wavelengths between 290–320 nm

UVC radiation: wavelengths less than 290 nm (narrow band wavelength)

DNA "building blocks": Four different nucleotides were found to be the "building blocks" in a DNA molecule (adenine, guanine, cytosine and thymine)

pyrimidine: Two of the four different building blocks in DNA—either cytosine or thymine pyrimidine dimer: a type of DNA damage which links together two pyrimidines adjacent to each other on the same strand of DNA (i.e. CC, CT, TC, or TT)

6,4 photoproduct or 6,4 pyrimidone: an example of DNA damage whereby two pyrimidines are linked together through a single bond between position 6 on one pyrimidine and position 4 on the second pyrimidine 5,6 photoproduct: also called "cis, syn cyclobutyl pyrimidine dimer (5,6)"—another example of DNA damage whereby two pyrimdines are linked together by a cyclobutyl (4 carbon ring) bond at both the 5 position and the 6 position of the pyrimidines ultraviolet light-induced photoproduct in DNA: a cyclobutyl pyrimidine dimer formed between adjacent pyrimidines on the same DNA strand. Cyclobutyl pyrimidine dimers are major photoproducts formed upon irradiation of DNA with ultraviolet light.

EXAMPLES

The following examples are provided so as to enable those of ordinary skill in the art to make the compositions of the invention. These examples are not intended to limit the scope of what the inventor regards as the invention. Efforts have been made to ensure accuracy with respect to numbers used to characterize the measured conditions; however, some experimental errors and deviations may be present.

EXAMPLE 1

GENERAL METHOD EMPLOYED TO DETERMINE THE NUMBER OF PYRIMIDINE DIMERS FORMED AS A RESULT OF EXPOSURE TO UV RADIATION

This Example outlines the general method employed to determine the number of pyrimidine dimers formed as a result of exposure to UV radiation. FIG. 1 outlines the principles of pyrimidine dimer determination by the alkaline agarose gel method. DNA in situ (in the skin or in culture, in vitro, or in DNA sequences themselves) is exposed to UV radiation and then the DNA is extracted from the skin as described in standard DNA isolation protocols. DNA occurs in its supercoiled state (double stranded DNA) and pyrimidine dimers result in the DNA from exposing the DNA to UV radiation (pyrimidine dimers are defined as a type of DNA damage which links together two pyrimidines adjacent to each other on the same strand of DNA (i.e. CC, CT, TC, or TF)). The DNA is then treated with UV endonuclease (e.g. isolated from *Micrococcus luteus*) which makes a single strand nick adjacent to each pyrimidine dimer. The DNA is no longer supercoiled and now appears in its "relaxed" circle form. The UV endonuclease creates the nicks and from these nicks the number of *Micrococcus luteus* UV endonuclease sensitive sites per 1000 bases (ESSIkb) is determined (Sutherland, et al, *Two dimensional, computer controlled film scanner: quantitation of fluorescence from ethidium bromide stained DNA gels*, Nal. Biochem., 139:390–399 (1984)).

The endonuclease treated or untreated DNA is denatured by treatment with alkali and electrophoresed on an alkaline agarose gel along with molecular weight standard markers. After denaturation, the single stranded DNAs are separated according to molecular length by electrophoresis in an alkaline agarose gel. The lane on the left of FIG. 1 depicts DNA not treated with UV endonuclease—DNA that contains dimers but was not treated with endonuclease migrates as a higher molecular length band. The lane on the right of FIG. 1 depicts the endonuclease treated DNA—the same DNA after UV endonuclease treatment migrates as a heterogeneous, lower molecular length band when compared to the DNA not treated with endonuclease. The alkaline agarose gel protocol is detailed in Freeman et al (Steven E. Freeman, et al., *Pyrimidine Dimer Formation in Human Skin, Photochemistry and Photobiology*, 46(2):207–212 (1987)—herein incorporated by reference).

EXAMPLE 2

TEST OF FCG SPF #4 ON LAMBDA DNA USING A FS20 SUNLAMP (0.320 MA)

This Example tests the protective effects of FCG SPF #4 sunscreen on Lambda DNA using a FS20 sunlamp (0.320 mA) as the source of ultraviolet light. This Example tests whether FCG SPF #4 sunscreen protects lambda DNA from pyrimidine dimer formation thereby reducing the number of pyrimidine photoproducts as a direct result of UV Radiation exposure.

Figure 2A:
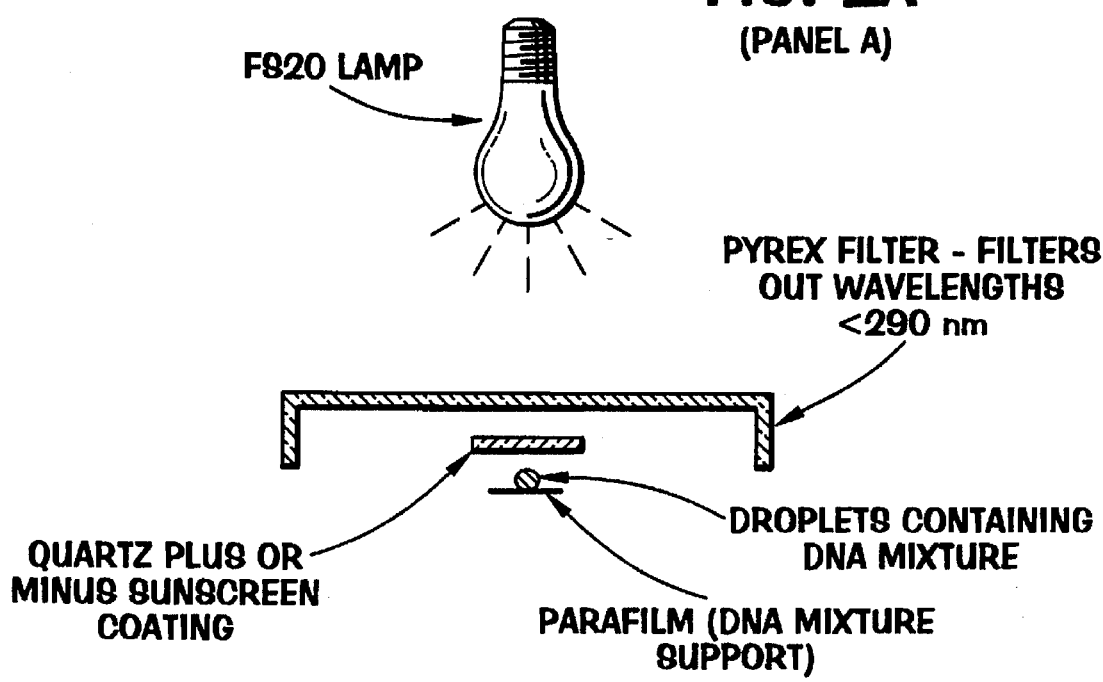
FIG. 2 Panel A: Experimental Set-up for Testing FCG SPF #4 in Reducing Pyrimidine Photoproducts in Lambda DNA Using a FS20 Sunscreening Lamp and a Pyrex Dish Filter (See FIG. 3). Panel B: Experimental Set-up for Testing FCG SPF #4 and Melanin Plus in Reducing Pyrimidine Photoproducts in 287-mer Exposed to UV Radiation (See FIG. 4).
Figure 2B:
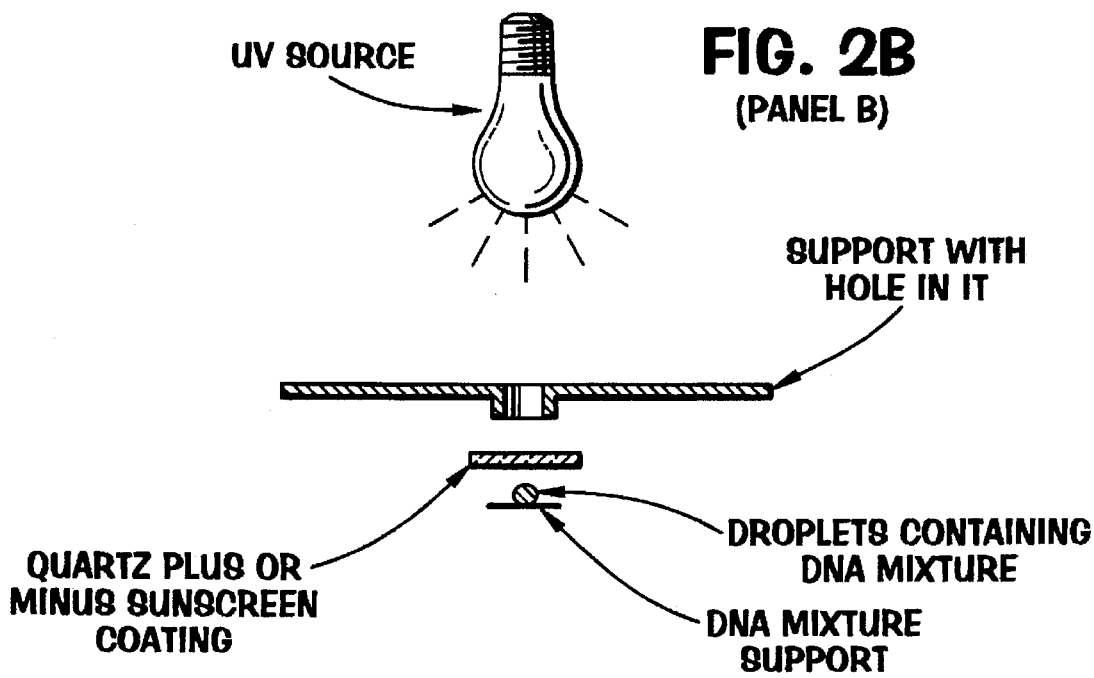

FIG. 2 (Panel A) depicts the experimental set-up for testing the protection SPF#4 can provide to DNA exposed to UV radiation. The Pyrex dish acts a filter to filter out wavelengths less than 290 nm. The quartz disk either was or was not coated with the sunscreen ("sunscreen plus" or "SS+" vs "sunscreen minus" or "SS–") and is placed between the filter dish and the DNA droplet. The DNA droplet is exposed to UV radiation for a predetermined amount of time which was calculated to induce a specific number of pyrimidine dimers.

In this Example, alkaline agarose gels are used to determine the number of pyrimidine dimers formed as a result of UV radiation exposure. This gel method is described in Example 1 and is only summarized here:

Step 1: Irradiated DNA using FS20 Lamp and a Pyrex dish filter. Lambda DNA was used in this Example and it is approximately 49.5 kilobases in size. The Pyrex dish was used to filter out wavelengths less than 290 nm. A quartz disk was placed between the filter and the DNA droplet. The quartz disk was either coated with the sunscreen or buffer only.

Step 2: Samples were removed at different times to obtain different exposure times which equate to a pre-calculated number of induced pyrimidine dimers.

Step 3: Add MLE (*Micrococcus lutues* endonuclease) to half of each reaction mixture to create a nick the single stranded DNA next to where the pyrimidine dimer was located. The other half of the reaction mixture received only buffer—no MLE).

Step 4: The DNA was analyzed on an alkaline agarose gel (Freeman S. E., et al, Photochemistry and Photobiology, 46(2):207–212 (1986) and data was plotted as described in FIG. 3.

FIG. 3 presents the data obtained from testing the protection of SPF #4 sunscreen on the formation of pyrimidine dimers in lambda DNA. The X-axis of FIG. 3 represents "Time" that Lambda n6 methanol-free DNA was exposed to a standard FS20 Fluorescent Sunscreen Tanning Lamp (to induce pyrimidine dimers). The Y-axis of FIG. 3 represents the number of endonuclease sensitive sites (ESS) per mega bases (number of pyrimidine dimers per mega (million) bases) as described below. The results from this experiment indicate that SPF #4 reduced the number of endonuclease sensitive sites thereby reducing the number of induced pyrimidine dimers. Thus, SPF#4 reduced the number of photoproducts which resulted from UV radiation exposure and which correlated with the number of induced pyrimidine dimers.

EXAMPLE 3

GENERAL METHODOLOGY FOR SITE-SPECIFIC LESION QUANTITATION IN UNSHIELDED AND MELANIN FCG SUNSCREEN-PROTECTED DNA

Human hazards of solar ultraviolet exposure include sunburn, premature skin aging and skin cancer, and DNA is a primary target for such damages. Much is known about the formation and repair of DNA damages at genomic and specific gene levels, but little is known of damage induction and repair at specific DNA sites. This Example was designed to evaluate the ability of sunscreening products manufactured by FCG, Inc. to protect against specific DNA damages at the specific nucleotide sequence level. Methods have been developed to detect and quantitate such damage formulation, as well as its reduction in the presence of sunscreens. The levels of cyclobutyl pyrimidine dimers (lethal, potentially carcinogenic) and pyrimidine (6-4) pyrimidone photoproducts (mutagenic) have been tested, and overall qualitative results indicate that Melanin Plus (Sun Protection Factor 4) and Melanin FCG sunscreening product protects against induction of such damages.

In general, an oligonucleotide via the standard protocol of polymerase chain reaction ("PCR:" a process for amplifying nucleic acid covered by U.S. Pat. Nos. 4,683,195 and 4,683,202). For example, a 287-mer was produced which comprises 287 base pairs from T-7 bacteriophage DNA inserted into a plasmid. Each 287-mer is labelled at its 3' end with P-32 ($^{32}P$). The DNA is then exposed to ultraviolet radiation in order to induce a pyrimidine dimer in the DNA. To do this, the DNA is exposed to a fixed amount of ultraviolet radiation (254 nm wavelength) for different predetermined times. The desired end result from the UV radiation exposure for each 287-mer is to induce either no pyrimidine dimers or at most to induce only one pyrimidine dimer. In order to determine the time to expose the DNA sequence to, a dose-rate meter is employed ("The Jagger Meter", Jagger, J., *A small and inexpensive ultraviolet dose-rate meter useful in biological experiments*, Radiat. Res. 14:394–403 (1961)). A meter reading from where the DNA sequence is positioned from the source of the radiation is determined (i.e. 111 microamps/sec/$m^2$) and this meter is pre-calibrated against a National Bureau of Standards Lamp. The calibration factor for the lamp employed for the instant invention is 22 microamps/sec/$m^2$ which equates to 1 Joule/sec/$m^2$. Every second of exposure is equal to 5 Joules; thus an exposure time of 110 seconds is equal to 550 Joules.

After the pre-determined exposure time, a sample of the reaction mixture is removed. A portion of this sample is then subjected to UV endonuclease. Next, part of the DNA is treated with UV endonuclease (e.g. an endonuclease isolated from *Micrococcus luteus*) which makes a single strand nick adjacent to each pyrimidine dimer. UV endonuclease is prepared by the standard protocol of Carrier et al (Carrier, W. L. *Endonuclease from Micrococcus luteus which has activity toward ultraviolet-irradiated DNA: purification and properties*, J. Bact. 102:178–186 (1970); See description regarding FIG. 1 above). The UV endonuclease creates nick adjacent to the dimer and from these nicks the number of *Micrococcus luteus* UV endonuclease sensitive sites per 1000 bases (ESS/kb) is determined (Sutherland, et al, *Two dimensional, computer controlled film scanner: quantitation of fluorescence from ethidium bromide stained DNA gels*, Nal. Biochem., 139:390–399 (1984)). Thus, if there are any pyrimidine dimers (i.e. CC, CT, TC, or TT) and if the DNA-mer is treated with UV endonuclease then the enzyme will induce or cause a cut in the single strand of DNA adjacent to where the pyrimidine dimer was located. The MLE reactions are performed at room temperature for one hour. The MLE reactions are stopped after one hour and the samples are stored −20° C. overnight. The endonuclease treated or untreated DNA is next subjected to a standard sequencing gel. Dye is added to sample, the sample is denatured by heat and then the sample is iced down prior to loading it on the gel. The protocols for these gels are standard and known to those skilled in the art but the following is an example of which method that could be used to achieve the same results: the DNA is analyzed on an 8% urea-containing polyacrylamide gel with G+A and C+T Maxam and Gilbert sequencing reactions as markers. Each sample is loaded onto this 8% sequencing gel and the gels were then autoradiographed (for approximately 48 hours). Bands were cut from the polyacrylamide gels and can be analyzed by the Cerenkov counting method. With this method, the data is corrected for multiple cuts within the same DNA fragment as described in Gordon et al (Gordon et al, J. Biol. Chem. 255:12047–12050 (1980)) and the percentage of initial molecules carrying scissions at a specific site were calculated. This is described in Brash et al (Brash, et al, Nature, 298:189–192 (1982)).

The data can be visually analyzed and/or analyzed via a computer. In order to visually analyze the gels, the same number of counts per minute (cpms) need to be loaded into each lane. The total cpms are calculated for each lane and the cpms per band are also determined. The percentage of cpms in each band is calculated and is compared to the total cpms in that lane by dividing the number of cpms per band by the total number of cpms in the lane. A computer software program is being developed at Brookhaven National Laboratories for quantitating the cpms per band as compared to the total cpms in each lane. Visually, each band can be compared to a comparable and receiving the same amount of Joules. Conclusions may be drawn if it is assumed that the same amount of cpms per lane were added to each lane.

EXAMPLE 4

254 NM IRRADIATION OF P-32 LABELLED 287-MER

This Example studied the effects of 254 nm Irradiation had on 32P labelled 287-met with or without FCG sunscreens. It attempted to answer the question Do FCG Sunscreens Protect or Reduce Pyrimidine Photoproducts? Thus, the purpose of this Example was to determine if either FCG Sunscreen or SPF #4 Sunscreen (Both products are available from Frances C. Gaskin, Inc.) protected DNA from the formation of pyrimidine dimers. If the sunscreens protected the DNA then it once can conclude that the sunscreens used reduced the number of pyrimidine photoproducts resulting from UV radiation exposure.

The protocol employed is presented in Example 3. As described in Example 3, a quantitative method for measuring site-specific levels of DNA lesions was used. Briefly, defined-sequence oligonucleotides are end-labeled on one strand by PCR using a $^{32}$P-labeled primer. The oligonucleotides, either unshielded or protected by a sunscreen, are exposed to narrow band radiation or sunlight, treated with lesion-specific agents to induce a nick at each lesion site, electrophoresed on sequencing gels along with sequence and size standards (Brash and Hazeltine, 1982, Nature, 298:189—Herein incorporated by reference). Radioactivity at each position is quantitated using a PhosphorImager. Use of the *Micrococcus luteus* UV endonuclease or T4 endonuclease V allows measurement of kinetics of induction of cyclobutyl pyrimidine dimers including C-C, C-T and T-T at individual sites in the oligonucleotide. This method allows determination of quantitative and qualitative changes in the lesion spectrum of DNA protected by sunscreening agents such as Melanin FCG (used interchangeably with "FCG") and SPF #4. The experimental set-up for testing FCG SPF #4 and Melanin Plus in reducing pyrimidine photoproducts in 287-met exposed to UV radiation (See FIG. 4) is shown in FIG. 2, Panel B.

The chart below presents the experimental details used for this Example. As described above, a 287-mer isolated from T-7 bacteriophage was used and the amount of 287-mer per dose 4ul (Column 1). Column 2 indicates whether Buffer only or Sunscreen ("SS") was added to each sample. Column 3 indicates the desired number of pyrimidine dimers ("Py D") for each sample (e.g. "0.2" means "20%" which means that there is one pyrimidine dimer per five (5) 287-mers). Column 4 is the amount of UV radiation dose (in Joules) which is needed to achieve desired number of pyrimidine dimers per 287-mer pyrimidine dimers in Column 3. The figure in Column 4 is pre-calculated such that the UV radiation given will induce the desired number of pyrimidine dimers shown in Column 3. Column 5 indicates the amount of UV exposure time, in seconds, to achieve the desired dose shown in Column 4.

| Col. 1 DNA | Col. 2 Sun Screen (SS) or Buffer Only | Col. 3 Dose Py D per molec | Col. 4 Dose Joules per m$^2$ | Col. 5 Time 111 uA per sec per m$^2$ |
|---|---|---|---|---|
| NO SUN SCREEN | | | | |
| 20 ul | Buffer | 0 | 0 | |
| 4 ul | Buffer | .2 | 110 | 22 sec |
| 4 ul | Buffer | .3 | 165 | 33 sec |
| 4 ul | Buffer | .4 | 220 | 44 sec |
| 4 ul | Buffer | .5 | 275 | 55 sec |
| SPF #4 | | | | |
| 4 ul | SS | .3x | | 33 sec |
| 4 ul | SS | .5x | | 55 sec |
| 4 ul | SS | 1.0x | | 110 sec |
| FCG Melanin | | | | |
| 4 ul | SS | .3x | | 33 sec. |

-continued

| Col. 1 DNA | Col. 2 Sun Screen (SS) or Buffer Only | Col. 3 Dose Py D per molec | Col. 4 Dose Joules per m² | Col. 5 Time 111 uA per sec per m² |
|---|---|---|---|---|
| 4 ul | SS | .5x | | 55 sec |
| 4 ul | SS | 1.0x | | 110 sec |
| 4 ul | SS | 1.5x | | 165 sec |

Continuing from the chart above, the chart below indicates the lane number for the DNA sequencing gel. The dose in Joules presented in the second column is the amount of UV radiation (254 nm) needed to induce the desired number of pyrimidine dimers shown in the third column. The column labelled "MLE Enz" indicates whether the specific gel lane received MLE or buffer only.

Figure 4:
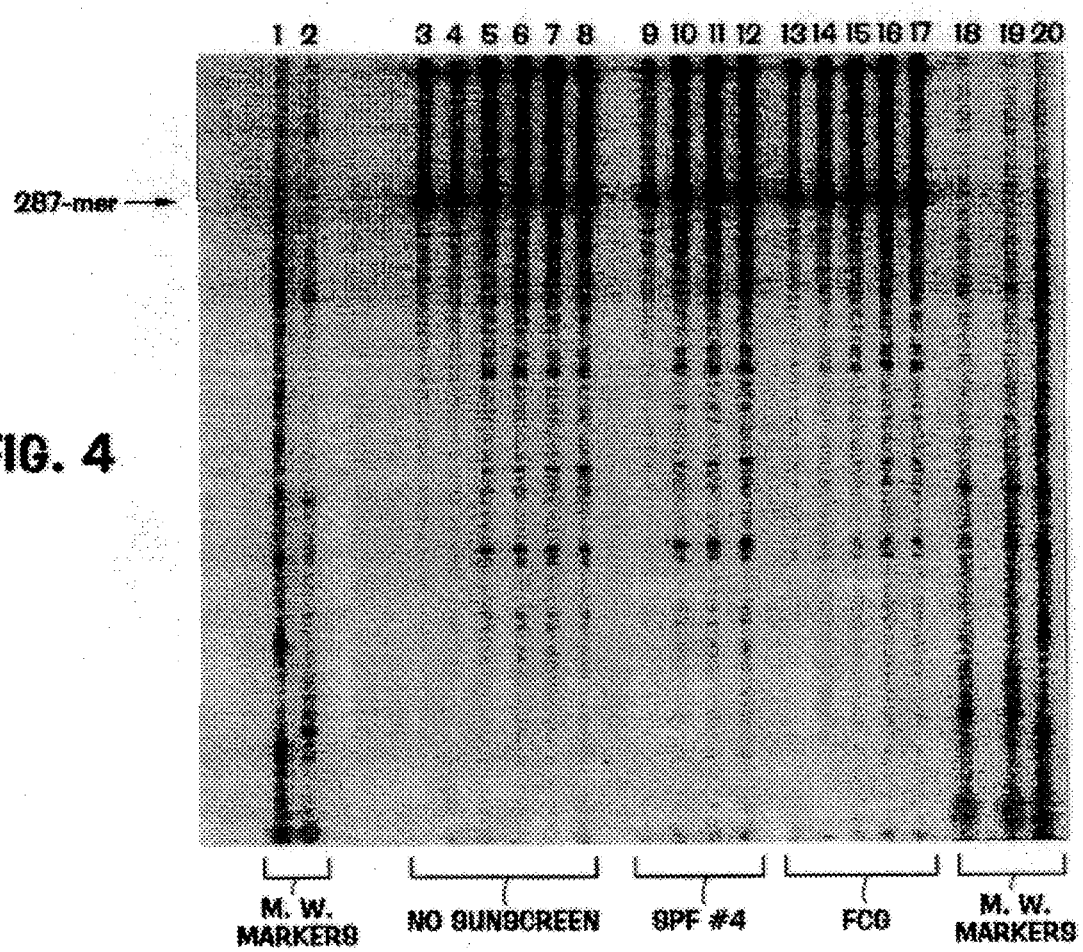
FIG. 4 Effects of 254 nm Irradiation on 32P Labelled 287-mer With or Without FCG Sunscreens. Do FCG Sunscreens Protect or Reduce Pyrimidine Photoproducts? See Panel B, FIG. 1 above for Experimental Set-up.

The data from this sequencing gel is shown in FIG. 4. The Joules given per lane is indicated below:

LANES 1–2 MOLECULAR WEIGHT MARKERS:

Lane 1: Molecular Weight Marker
Lane 2: Molecular Weight Marker

LANES 3–8: NO SUNSCREEN

Lane 3: No UV
Lane 4: No UV
Lane 5: 110 J/m²
Lane 6: 165 J/m²
Lane 7: 220 J/m²
Lane 8: 275 J/m²

LANES 9–12: SPF #4 (0.005 G/2.5 CM²)

Lane 9: No UV
Lane 10: 165 J/m²
Lane 11: 220 J/m²
Lane 12: 275 J/m²

LANES 13–17: FCG (1:500 DILUTION OF PURE FCG)

Lane 13: No UV
Lane 14: 165 J/m²
Lane 15: 275 J/m²
Lane 16: 550 J/m²
Lane 17: 825 J/m²

LANES 18–20 MOLECULAR WEIGHT MARKERS:

Lane 18: Molecular Weight Marker
Lane 19: Molecular Weight Marker
Lane 20: Molecular Weight Marker Higher doses were used when the UV radiation had to go through a sunscreen. This was done in order to insure that some pyrimidine dimers could be observed.

The results from this experiment are shown in FIG. 4. The control in lanes 3 and 4 showed no bands migrating under the 287-mer band (indicated with the arrow); thus, both UV radiation and endonuclease are essential to observe bands below the 287-mer band. In lanes 5–8—NO SUNSCREEN (yes UV and yes endonuclease) smaller bands appeared below the 287-mer band which is indicative of pyrimidine dimers being present. In lanes 9–12, the sunscreen SPF #4 was used with higher overall UV doses in Joules as compared to lanes 3–8. Note that there are no bands below the 287-mer in Lane 9; this is because there was no UV given to that sample and as stated above, both UV radiation and endonuclease are needed to see bands below the 287-mer which indicate the presence of pyrimidine dimers. The results with SPF #4 Sunscreen are harder to quantify when comparing the band number and intensity in lane 6 with those in lane 10. The SPF #4 data will have to be computer analyzed prior to drawing any conclusions. It can be concluded that some UV goes through the SPF #4 sunscreen but how much can not be answered at this time. The same general statements apply when comparing the band number and intensity for lane 8 and lane 11.

FCG Sunscreen was used in lanes 13–17. Lane 13 (no UV and yes enzyme) demonstrated what a good control would look like. Note that there are no clear bands smaller than the 287-met band. Because of the different doses used in these lanes with the FCG sunscreen, lanes 6 (no sunscreen, 165 J) and 14 (FCG sunscreen, 165 J) can be compared, and lanes 8 (no sunscreen, 275 J) and 15 (FCG sunscreen, 275 J) can be compared. It is apparent that the intensity of the bands in lane 14 is less than the intensity of the bands in lane 6. Also, the intensity of the bands in lane 15 is less than the intensity of the bands in lane 8. From this data, one could conclude that if the total number of cpms in 5, 6, 7, or 8 was equal to the cpms in lanes 14–17, then FCG sunscreen does indeed protect the 287-mer from UV induced pyrimidine dimers. Thus, FCG can reduce the number of pyrimidine photoproducts as compared to the controls. These data will be computer analyzed in order to quantify this data.

| Lane # | Dose Joules 254 nm | UV # Py DIMERS | MLE Enz | |
|---|---|---|---|---|
| 1 | — | — | | MW MARKER |
| 2 | — | — | | MW MARKER |
| 3 | 0 | NONE | NONE | |
| 4 | 0 | NONE | MLE | |
| 5 | 110 J | .2 Py D | MLE | |
| 6 | 165 J | .3 Py D | MLE | |
| 7 | 220 J | .4 Py D | MLE | |
| 8 | 275 J | .5 Py D | MLE | |
| 9 | 0 | NONE | MLE | |
| 10 | 165 J | .2X | MLE | |
| 11 | 275 J | .5X | MLE | |
| 12 | 550 J | 1.0X | MLE | |
| 13 | 0 | NONE | MLE | |
| 14 | 165 J | 33 SEC | MLE | |
| 15 | 275 J | 55 SEC | MLE | |
| 16 | 550 J | 110 SEC | MLE | |
| 17 | 825 J | 165 SEC | MLE | |
| 18 | — | | | MW MARKER |
| 19 | — | | | MW MARKER |
| 20 | — | | | MW MARKER |

EXAMPLE 5

UV-PROTECTIVE EFFECTS OF MELANIN PLUS AND MELANIN FCG ON HUMAN SKIN

The objective of this example is to use sunscreen compounds manufactured by Frances Christian Gaskin, Inc. to study the effects ultraviolet light has on human skin. The above protocols and experiments will be performed on human skin order to quantify the reduction (and protection) of pyrimidine photoproducts as a result of exposure of UV radiation through the sunscreen.

EXAMPLE 6

UV-PROTECTIVE EFFECTS OF MELANIN PLUS AND MELANIN FCG ON HUMAN SKIN CELLS

The objective of this Example is to use sunscreen compounds manufactured by Frances Christian Gaskin, Inc. to study the effects ultraviolet light has on human skin cells in vitro. These studies will allow selection and or creation of more efficient sun preparations and may indicate modifications to current preparations for higher efficacy.

More specifically, this Example is directed to studying the effects of UV in the presence and absence of FCG sunscreens on human cultured cells in vitro, including melanocytes. In general, for measurement of DNA damage, cells will be exposed to broad spectrum, or narrow band UVC (wavelengths less than 290 nm), UVB (290–320 nm) or UVA (320–400 nm) [monitored with a spectral radiometer] in the absence or presence of sunscreens at different concentrations. The cells will be harvested, the DNA isolated, treated with a lesion-specific agent, electrophoresed, a quantitative electronic image obtained, data stored on an optical disk, and computer-aided analysis carried out to obtain frequency of different kinds of DNA lesions.

Studying Survival and Mutation Rates

Once these results are analyzed, further studies will be performed to study survival and mutation rates (including transformation) as a result of UV exposure of cells in the absence or presence of different levels of sunscreen. The cells would then be plated under permissive conditions to determine survival or under non-permissive conditions to select for specific mutations or transformation. After incubation allowing for cell growth, the survival, mutation or transformation frequencies would be determined by scoring microscopically either manually or by using electronic imaging and computer-assisted scoring.

The protective effects on DNA at the molecular level due to the sunscreening preparations will be studied two different ways:

(1) Determination of the level of screening of DNA damages by the sunscreens in human skin cells;

(2) Measurement of the kinds of damages produced by UV in the absence and presence of sunscreens.

The inventor anticipates that the sunscreen preparations will be effective in shielding DNA in human skin cells against UV.

EXAMPLE 7

UV-PROTECTIVE EFFECTS OF MELANIN PLUS AND MELANIN FCG ON HUMAN SKIN MODEL SYSTEMS

The objective of this Example is to use sunscreen compounds manufactured by Frances Christian Gaskin, Inc. to study the effects ultraviolet light has on human skin model systems. The experiments and protocols as described above will be employed in the Example.

EXAMPLE 8

UV-PROTECTIVE EFFECTS OF MELANIN PLUS AND MELANIN FCG ON HUMAN SKIN IN VIVO

The objective of this example is to use sunscreen compounds manufactured by Frances Christian Gaskin, Inc. to study the effects ultraviolet light has on human skin in vivo.

The experiments and protocols as described above will be employed in the Example.

EXAMPLE 9

QUANTITATION OF DATA

This Example is designed to quantitate the data generated from these experiments. Software is being developed to allow accurate quantitation of the data obtained in these experiments. Commercially available software only provides crude estimates of lesion levels, thus a reliable computer is needed. The level of several pyrimidine dimers and 6-4 photoproducts at different sites in the DNA, and in different sequence contexts, will be determined. The level of shielding against such photoproducts will be compared with the degree of protection against erythema.

REFERENCES

The following references may facilitate the understanding or practice of certain aspects of the present invention. Inclusion of a reference in this list is not intended to and does not constitute an admission that the reference represents prior art with respect to the present invention.

1. Steven E. Freeman, et al., *Pyrimidine Dimer Formation in Human Skin*, Photochemistry and Photobiology, Vol. 46 (No. 2): 207–212 (1987).
2. Douglas E. Brash & William A. Haseltine, *UV-induced Mutation Hotspots Occur at DNA Damage Hotspots*, Nature, Vol. 298: 189 (1982).
3. Gaskin, Composition and Method for Protecting the Skin from UV-Rays, U.S. Pat. No. 5,256,403, Issued Oct. 26, 1993.
4. Gaskin, *Sun Protectant Composition and Method*, U.S. Pat. No. 4,806, 344, Issued Feb. 21, 1989.
5. John Clark Sutherland, et al., *Unidirectional Pulsed-Field Electrophoresis of Single and Double-Stranded DNA in Agarose Gels; Analytical Expressions Relating Mobility and Molecular Length and Their Application in the Measurement of Strand Breaks*, Analytical Biochemistry, Volume 162: 511–520 (1987).
6. S. E. Freman, et al., *Wavelength Dependence of Pyrimidine Dimer Formation in DNA of Human Skin Irradiated in situ with Ultraviolet Light*, Proc. Nat'l. Acad. Sci. USA Vol. 86: 5605–5609 (1989).
7. Steven E. Freeman, et al., *Quantitation of Radiation, Chemical or Enzyme-Induced Single Strand Breaks in Nonradioactive DNA by Alkaline Gel Electrophoresis: Application to Pyrimidine Dimers*, Analytical Biochemistry, Vol. 158: 119–129 (1986).
8. Betsy M. Sutherland and Alice G. Shih, *Quantitation of Pyrimidine Dimer Contents of Nonradioactive Deoxyribonucleic Acid by Electrophoresis in Alakaline Ariarose Gels*, Biochemistry, Vol. 22: 745–749 (1983).
9. John C. Sutherland, et al., *Lesion Measurement in Non-Radioactive DNA by Quantitative Gel Electrophoresis*, DNA Damage and Repair in Human Tissues, 45–61 (1990).
10. J. C. Sutherland, et al., *Quantitative Electronic Imaging of Gel Fluorescence with CCD Cameras: Applications in Molecular Biology*, BioTechniques, Vol. 10 (No. 4): 492–497 (1991).
11. F. E. Quaite, B. M. Sutherland & J. C. Sutherland, *Action Spectrum for DNA Damage in Alfalfa Lowers Predicted Impact of Ozone Depletion*, Nature, Vol. 358: 576–578 (1992).
12. Paula V. Bennett and Betsy M. Sutherland, *Quantitative Detection of Single-Copy Genes in Nanogram Samples of*

*Human Genomic DNA, BioTechniques*, Vol. 15 (No. 3): 520–525 (1993).

13. F. E. Quaite, J. C. Sutherland and B. M. Sutherland, *Isolation of High-Molecular-Weight Plan DNA for DNA DamaRe Quantitation: Relative Effects of Solar 297 nm UVB and 365 nm Radiation, Plant Molecular Biology*, Vol. 24: 475–483 (1994).

14. R. Cadi, et al., *Protective Effect of Flavopherol Against Lipid Peroxidation and Experimental UV B-induced Carcinogenesis in the Hairless Mouse, Nouv. Dermatol*

15. J. C. Sutherland, Electronic Imaging of Electrophoretic Gels and Blots, VCH Publishers, 1–42 (1993).

16. Sutherland, et al, *Two dimensional, computer controlled film scanner: quantitation of fluorescence from ethidium bromide stained DNA gels, Nal.* Biochem., 139:390–399 (1984).

17. Carrier, W. L. Endonuclease from *Micrococcus luteus which has activity toward ultraviolet-irradiated DNA: purification and properties*, J. Bact. 102:178–186 (1970).

18. Jagger, J., *A small and inexpensive ultraviolet dose-rate meter useful in biological experiments*, Radiat. Res. 14:394–403 (1961).

Additional advantages and modifications will be readily apparent to those skilled in the art. The invention in its broader aspects is therefore not limited to the specific details or representative examples described. Thus, the foregoing description has been directed to particular embodiments of the invention in accordance requirements to the Patent Statues for the purposes of illustration and explanation. It will be apparent, however, to those skilled in this art, that many modifications, changes, and variations in the claimed invention, including, but not limited to, compositions, solutions, methods, etc. set forth will be possible without departing from the scope and spirit of the claimed invention. It is intended that the following claims be interpreted to embrace all such modifications, variations, and changes.

What is claimed is:

1. A method for reducing pyrimidine dimer formation in human skin comprising the step of:

a) applying an effective amount of melanin to human skin, wherein said melanin is in an amount effective to reduce pyrimidine dimer formation, and wherein said melanin is in a vehicle suitable for topical application.

2. The method of claim 1 wherein said vehicle is an ointment, cream, or lotion.

3. A method for reducing pyrimidine dimer formation in human skin comprising the step of:

a) applying an effective amount of solubilized melanin to human skin, wherein said melanin is in an amount effective to reduce pyrimidine dimer formation, and wherein said substance for solubilizing melanin is selected from the group consisting of triethanolamine and trypsin, wherein said solubilizing substance is present in an amount sufficient to solubilize the melanin, wherein said melanin and solubilizing substance is in a vehicle suitable for topical application.

4. The method of claim 3 wherein said vehicle is an ointment, cream, or lotion.

5. A method for monitoring levels of pyrimidine dimer formation in human skin comprising of the steps of:

a) measuring the amount of pyrimidine dimers in human skin prior to applying an effective amount of melanin thereto;

b) applying an effective amount of melanin to said human skin, wherein said melanin is in an amount effective to reduce pyrimidine dimer formation, and wherein said melanin is in a vehicle suitable for topical application.

c) measuring the level of pyrimidine dimers located in said human skin after applying an effective amount of melanin thereto, and exposure of said human skin to ultraviolet radiation.

6. The method of claim 5 wherein said vehicle is an ointment, cream, or lotion.

7. A method for monitoring levels of pyrimidine dimer formation in human skin comprising the steps of:

a) measuring the amount of pyrimidine dimers in human skin prior to applying an effective amount of solubilized melanin thereto, wherein said melanin is in an amount effective to reduce pyrimidine dimer formation, and wherein said substance for solubilizing melanin is selected from the group consisting of triethanolamine and trypsin, wherein said solubilizing substance is present in an amount sufficient to solubilize the melanin, said melanin and solubilizing substance being in a vehicle suitable for topical application;

b) applying an effective amount of the solubilized melanin to said human skin;

c) measuring the level of pyrimidine dimers located in said human skin after applying an effective amount of the solubilized melanin to said human skin, and exposure of said human skin to ultraviolet radiation.

8. The method of claim 7 wherein said vehicle is an ointment, cream, or lotion.

* * * * *